(12) United States Patent
Savord

(10) Patent No.: US 9,983,176 B2
(45) Date of Patent: May 29, 2018

(54) TWO DIMENSIONAL ULTRASOUND TRANSDUCER ARRAYS OPERABLE WITH DIFFERENT ULTRASOUND SYSTEMS

(71) Applicant: KONINKLIJKE PHILIPS N.V., Eindhoven (NL)

(72) Inventor: Bernard Joseph Savord, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 248 days.

(21) Appl. No.: 14/408,382

(22) PCT Filed: Jun. 18, 2013

(86) PCT No.: PCT/IB2013/054988
§ 371 (c)(1),
(2) Date: Dec. 16, 2014

(87) PCT Pub. No.: WO2014/001962
PCT Pub. Date: Jan. 3, 2014

(65) Prior Publication Data
US 2015/0241397 A1   Aug. 27, 2015

Related U.S. Application Data

(60) Provisional application No. 61/665,571, filed on Jun. 28, 2012.

(51) Int. Cl.
*G01N 29/34* (2006.01)
*G01S 15/89* (2006.01)
(Continued)

(52) U.S. Cl.
CPC ......... *G01N 29/341* (2013.01); *A61B 8/4438* (2013.01); *A61B 8/4444* (2013.01);
(Continued)

(58) Field of Classification Search
CPC ...... A61B 8/00; G01N 29/00; G01N 2291/00; G01S 7/00; G01S 15/00
See application file for complete search history.

(56) References Cited

U.S. PATENT DOCUMENTS 5,229,933 A    7/1993 Larson
5,520,187 A *  5/1996 Snyder ................ G01S 7/52034
                                                    600/447
(Continued)

FOREIGN PATENT DOCUMENTS

DE       19741361       4/1999
WO    2007099473 A1    7/2007
(Continued)

*Primary Examiner* — Katherine Fernandez
*Assistant Examiner* — Sean D Mattson

(57) ABSTRACT

A matrix array transducer probe has a two dimensional array of transducer elements coupled to adjustable delays for each element. A controllable switch matrix combines a plurality of differently delayed element signals to form a patch signal and produces a plurality of patch signals in this manner. The switch matrix determines the patch configuration in consideration of the number of channels of a system beamformer which completes the beamformation, and the element delays are set in consideration of the configuration of the elements to be used in each patch. Patch signal formation may be done in two stages, including a stage which includes a hard-wired signal combiner. The matrix array probe can be operated with differently sized system beamformers or the same transducer stack used in different probes configured for specific beamformer configurations.

12 Claims, 10 Drawing Sheets

(51) Int. Cl.
  *A61B 8/00*  (2006.01)
  *G01N 29/24*  (2006.01)
  *G01S 7/52*  (2006.01)

(52) U.S. Cl.
  CPC ............ *G01N 29/24* (2013.01); *G01S 7/5208* (2013.01); *G01S 15/89* (2013.01); *G01S 15/8927* (2013.01); *G01N 2291/028* (2013.01); *G01N 2291/106* (2013.01); *G01S 15/8915* (2013.01)

(56) References Cited

U.S. PATENT DOCUMENTS

| | | | |
|---|---|---|---|
| 5,997,479 A | 12/1999 | Savord et al. | |
| 6,013,032 A | 1/2000 | Savord | |
| 6,126,602 A | 10/2000 | Savord et al. | |
| 6,371,918 B1* | 4/2002 | Bunce | A61B 8/4281 600/458 |
| 7,517,317 B2 | 4/2009 | Lazenby et al. | |
| 7,927,280 B2 | 4/2011 | Davidsen | |
| 7,941,908 B2* | 5/2011 | Phelps | G01S 7/52023 29/594 |
| 2005/0148873 A1* | 7/2005 | Petersen | A61B 8/4438 600/447 |
| 2005/0192499 A1* | 9/2005 | Lazenby | G01S 15/8927 600/459 |
| 2005/0203392 A1* | 9/2005 | Peteresen | G01S 15/8927 600/437 |
| 2005/0251035 A1* | 11/2005 | Wong | A61B 8/00 600/437 |
| 2010/0049053 A1* | 2/2010 | Yamamoto | G01S 7/52084 600/459 |
| 2010/0298714 A1* | 11/2010 | Miyajima | A61B 8/06 600/459 |
| 2011/0172537 A1 | 7/2011 | Hongou et al. | |

FOREIGN PATENT DOCUMENTS

| | | | |
|---|---|---|---|
| WO | WO 2007099473 A1 * | 9/2007 | ........... G01S 7/5208 |
| WO | 2010055428 A1 | 5/2010 | |
| WO | 2013168045 A1 | 11/2013 | |

* cited by examiner

TWO DIMENSIONAL ULTRASOUND TRANSDUCER ARRAYS OPERABLE WITH DIFFERENT ULTRASOUND SYSTEMS This application is the U.S. National Phase application under 35 U.S.C. § 371 of International Application No. PCT/IB2013/054988, filed on Jun. 18, 2013, which claims the benefit of U.S. Provisional Application No. 61/665,571 filed on Jun. 28, 2012. These applications are hereby incorporated by reference herein.

This invention relates to medical diagnostic ultrasound systems and, in particular, to matrix array transducer probes operable with different ultrasound system beamformers.

Ultrasound array transducers may be configured as a single row of transducer elements, a one-dimensional (1D) array for imaging a two dimensional (2D) image plane, or as a two dimensional (2D) array of transducer element for imaging a three dimensional region. A 2D array comprises elements extending in both azimuth and elevation directions which can be operated fully independently to both focus and steer beams in any azimuth or elevation direction. These arrays can be configured in either flat or curved orientations. The present invention is directed to 2D array transducers which can steer and focus in both azimuth and elevation to scan both 2D image planes and three dimensional volumetric regions of interest.

Two dimensional array transducers and even 1D array with large numbers of elements pose a problem due to their large number of transducer elements. Since each of these elements must be individually controlled on transmit and receive, a separate signal line must be provided for each element. A 1D array may comprise a row of 100-200 elements, requiring 100-200 signal lines, which can be accommodated in a relatively small and light probe cable, but may need to operate with a system beamformer of relatively few channels. A 2D array may have 100-200 rows of elements in one dimension and 100-200 columns of elements in the other dimension, totaling thousands of individual elements. A cable of many thousands of signal lines is not practical for a probe which hand-held and must be manipulated by the sonographer. An implementation of the present invention overcomes these problems by use of a microbeamformer integrated circuit attached to the 2D array which performs partial beamforming of groups of elements referred to as patches. The individually delayed and summed signals from the elements of each patch are conducted over a standard size cable to the ultrasound system beamformer where the summed signal from each patch is applied to a channel of the system beamformer, which completes the beamforming operation. This partitioning of the full beamforming operation between a microbeamformer in the probe and the channels of the system beamformer, illustrated for instance in U.S. Pat. No. 5,229,933 (Larson, III), U.S. Pat. No. 5,997,479 (Savord et al.), U.S. Pat. No. 6,013,032 (Savord), and U.S. Pat. No. 6,126,602 (Savord et al.), enable the use of a cable with a relatively few number of signal lines between the probe and the ultrasound system.

An ultrasound probe is generally designed with a predetermined configuration that operates with a corresponding system beamformer configuration. A 64-element 1D array probe will operate with a 64-channel system beamformer and a 128-element array probe will operate with a 128-channel system beamformer, for instance. It would be desirable to have a probe with a variable configuration that is able to operate with different system beamformers. One approach to making a variable 2D array probe is shown in U.S. Pat. No. 7,517,317 (Lazenby et al.) In this patent the elements of a 2D array are divisible into blocks of elements which may be selectively connected together by switches so that the signals from multiple elements are combined onto a single output. A larger number of elements are connected together on a smaller number of outputs for a lower number of beamformer channels and a smaller number of elements are connected together on a larger number of outputs for a higher number of beamformer channels. The pitch of the array is affected by the number of elements connected together, however, which is the center-to-center spacing of adjacent groups of interconnected elements. When the pitch is increased the beam sidelobes increase, which increases clutter and decreases the clarity and resolution of the resultant image. The degree to which a beam may be steered and focused is also restricted. Accordingly it is desirable to be able to configure a 2D matrix array for operation with different system beamformers without these deleterious effects.

In accordance with the principles of the present invention, an ultrasonic matrix array transducer probe is operated with a microbeamformer to process signals from variable patches of transducer elements which are varied correspondence with the system beamformer with which the probe is to operate. The signal from each element is selectively delayed, with signals from elements to be used in the same patch being differently delayed in relation to a common time or phase reference for the patch. The differently delayed signals are combined to produce a microbeamformed patch signal. The number of patch signals formed in this way is also selectively controlled to correspond with the number of channels of the system beamformer used to complete the beamformation process. An implementation of the present invention enables the same matrix array stack with its microbeamformer to be used with different ultrasound systems or with the most cost-effective probe cable for the system.

Figure 1:
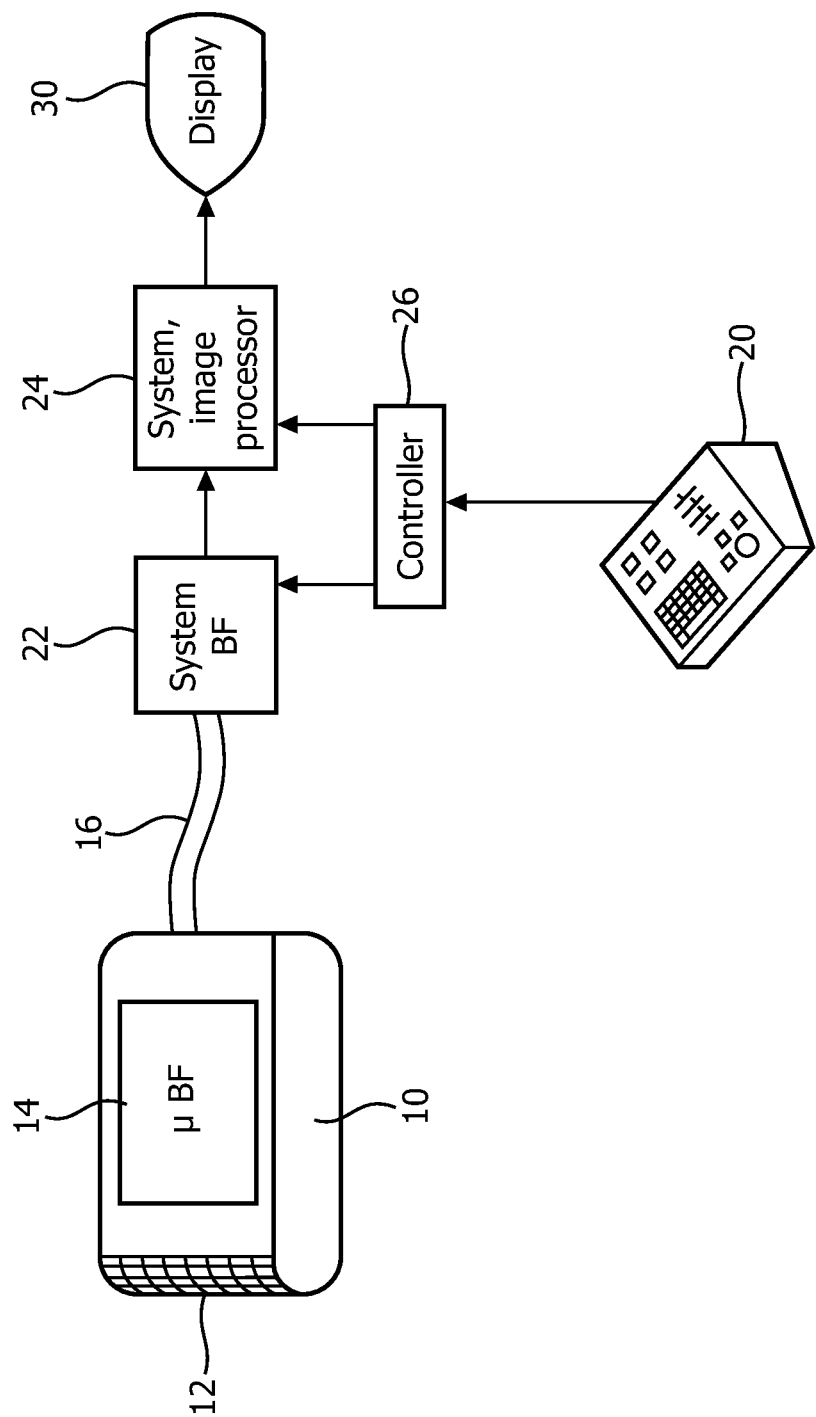
FIG. 1 illustrates in block diagram form a 2D curved array transducer and microbeamformer probe of the present invention.

Referring first to FIG. 1, an ultrasound system constructed in accordance with the principles of the present invention is shown in block diagram form. A probe 10 has a two dimensional array transducer 12 which in this example is curved in the elevation dimension such as that shown in U.S. Pat. No. 7,927,280 (Davidsen). The elements of the array are coupled to a microbeamformer 14 located in the probe behind the transducer array. The microbeamformer applies timed transmit pulses to elements of the array to transmit beams in the desired directions and to the desired focal points in the three dimensional image field in front of the array. Echoes from the transmitted beams are received by the array elements and coupled to delays of the microbeamformer 14 where they are individually delayed. The delayed signals of a group of transducer elements comprising a patch are combined to form a partial sum signal for the patch. As used herein the term "patch" refers to a group of transducer elements which are operated together and have their signals individually delayed in relation to a reference and then combined by the microbeamformer to form one signal for a probe conductor or an ultrasound system beamformer channel. In a typical implementation combining is done by coupling the delayed signals from the elements of the patch to a common bus, obviating the need for summing circuits or other complex circuitry. The bus of each patch is coupled to a conductor of a cable 16, which conducts the patch signal to the system mainframe. In the system mainframe the patch signals are digitized and coupled to channels of a system beamformer 22, which appropriately delays each patch signal. The delayed patch signals are then combined to form a coherent steered and focused receive beam. The beam signals from the 3D image field are processed by a signal and image processor 24 to produce 2D or 3D images for display on an image display 30. Control of ultrasound system parameters such as probe selection, beam steering and focusing, and signal and image processing is done under control of a controller 26 which is coupled to various modules of the system. In the case of the probe 10 some of this control information is provided from the system mainframe over data lines of the cable 16 as described more fully below. The user controls many of these operating parameters by means of a control panel 20.

Figure 2:
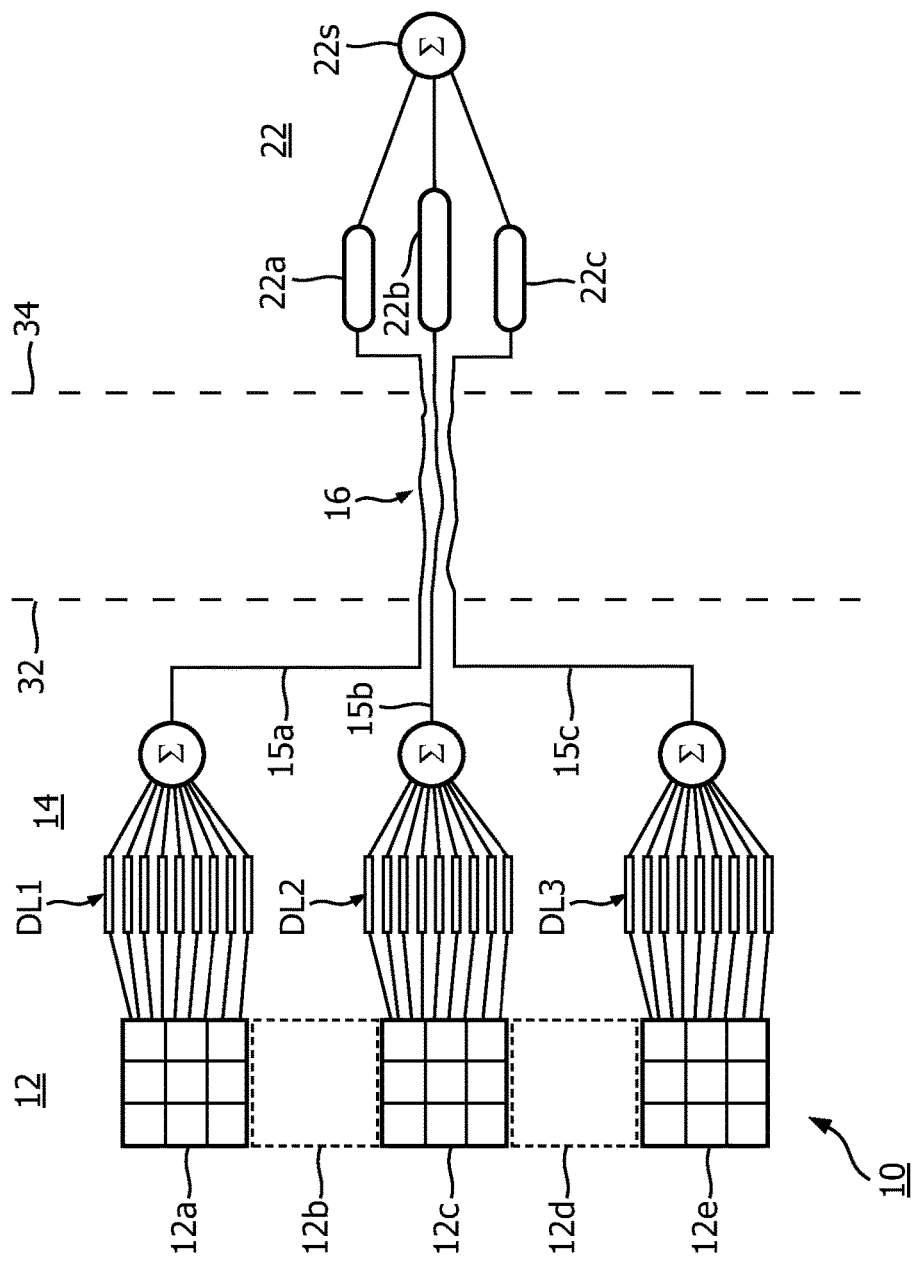
FIG. 2 is a block diagram illustrating the concept of a partial beamsum microbeamformer.

FIG. 2 illustrates the concept of a partially summing microbeamformer. The drawing of FIG. 2 is sectioned into three areas by dashed lines 32 and 34. Components of the probe 10 are shown to the left of line 32, components of the system mainframe are shown to the right of line 34, and the cable 16 is shown between the two lines. The two dimensional matrix array 12 of the probe is divided into patches of contiguous transducer elements. Five of the patches of the array 12 are shown in the drawing, each including nine neighboring elements. The microbeamformer channels for patches 12a, 12c, and 12e are shown in the drawing. The nine elements of patch 12a are coupled to nine delay lines of the microbeamformer indicated at DL1. Similarly the nine elements of patches 12c and 12e are coupled to the delay lines indicated at DL2 and DL3. The delays imparted by these delay lines are a function of numerous variables such as the size of the array, the element pitch, the spacing and dimensions of the patch, the range of beam steering, and others. The delay line groups DL1, DL2, and DL3 each delay the signals from the elements of their respective patch to a common time or phase reference for the patch. The nine delayed signals from each group of delay lines are then combined by a respective summer Σ to form a partial sum signal of the array from the patch of elements. Each partial sum signal is put on a separate bus 15a, 15b, and 15c, each of which is coupled to a conductor of the cable 16, which conducts the partial sum signals to the system mainframe. In the system mainframe each partial sum signal is applied to a delay line 22a, 22b, 22c of the system beamformer 22. These delay lines focus the partial sum signals into a common beam at the output of the system beamformer summer 22s. The fully formed beam is then forwarded to the signal and image processor for further processing and display. While the example of FIG. 2 is shown with 9-element patches, it will be appreciated that a constructed microbeamformer system will generally have patches with larger numbers of elements such as 12, 20, 48, or 70 elements or more. The elements of a patch can be adjacent to each other, be spaced apart, or even intermingled in a checkerboard pattern, with "odd" numbered elements combined in one patch and "even" numbered elements combined in another. The patches can be square, rectangular, diamond-shaped, hexagonal, or any other desired shape.

Figure 3:
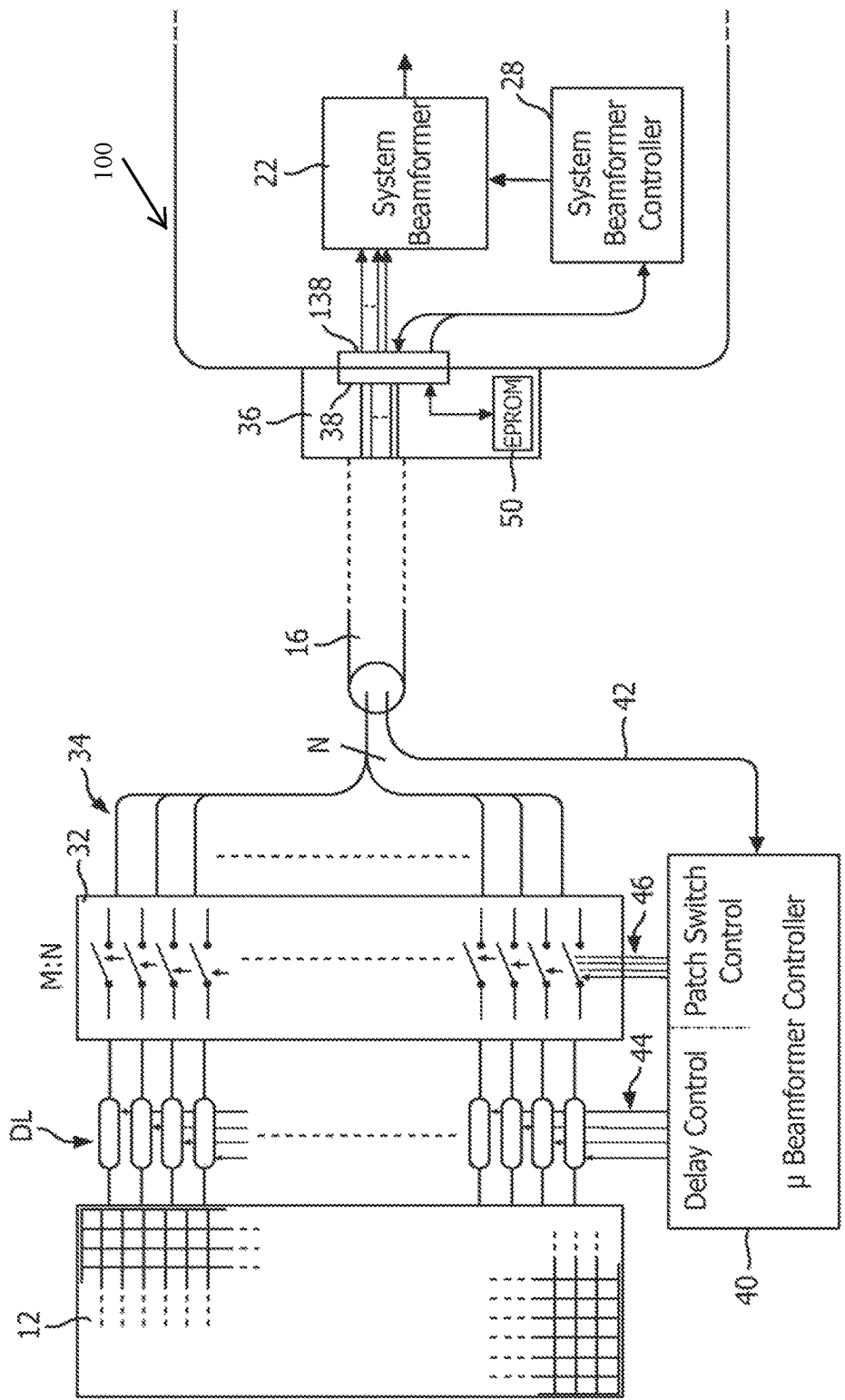
FIG. 3 illustrates a microbeamformer matrix array probe and ultrasound system constructed in accordance with the principles of the present invention.
Figure 7:
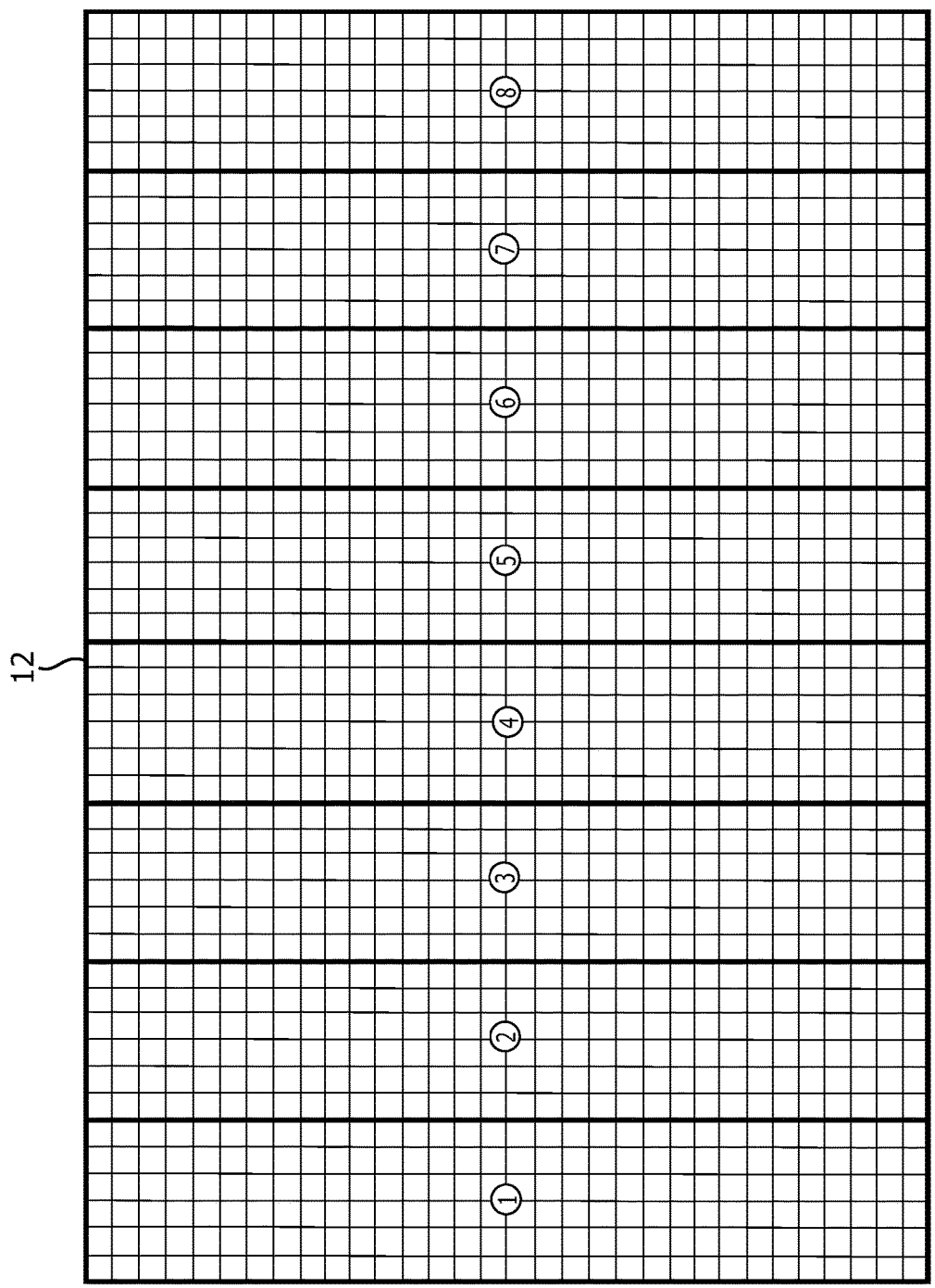
FIG. 7 illustrates a 2D matrix array transducer with uniformly sized patches for use with an 8-conductor cable or 8-channel system beamformer.

FIG. 3 illustrates a matrix array probe 10 and mainframe ultrasound system 100 constructed in accordance with the principles of the present invention. A two dimensional matrix array 12 has its individual transducer elements coupled to controllable delay lines DL of a microbeamformer 14. A microbeamformer controller 40 in the probe receives control signals over one or more lines 42. The microbeamformer controller applies control signals over lines 44 which set the delays of the delay lines DL for the transducer element signals. These delays are appropriate for the desired patch size and shape. The delayed transducer element signals are coupled to a switch matrix 32 which directs the signals from elements of the same patch to one output 34. For example it may be desired to combine the delayed signals of 192 elements to form a single patch signal as shown in FIG. 7 below. Switches of the switch matrix 32 are closed to connect delayed signals of the desired 192 elements onto a common bus. Switch closure, and thus patch configuration, is controlled by patch switch control signals on lines 46 provided by the microbeamformer controller 40. A very flexible switch matrix which enables any delayed element signal to be used in any patch is shown in FIG. 4.

Figure 4:
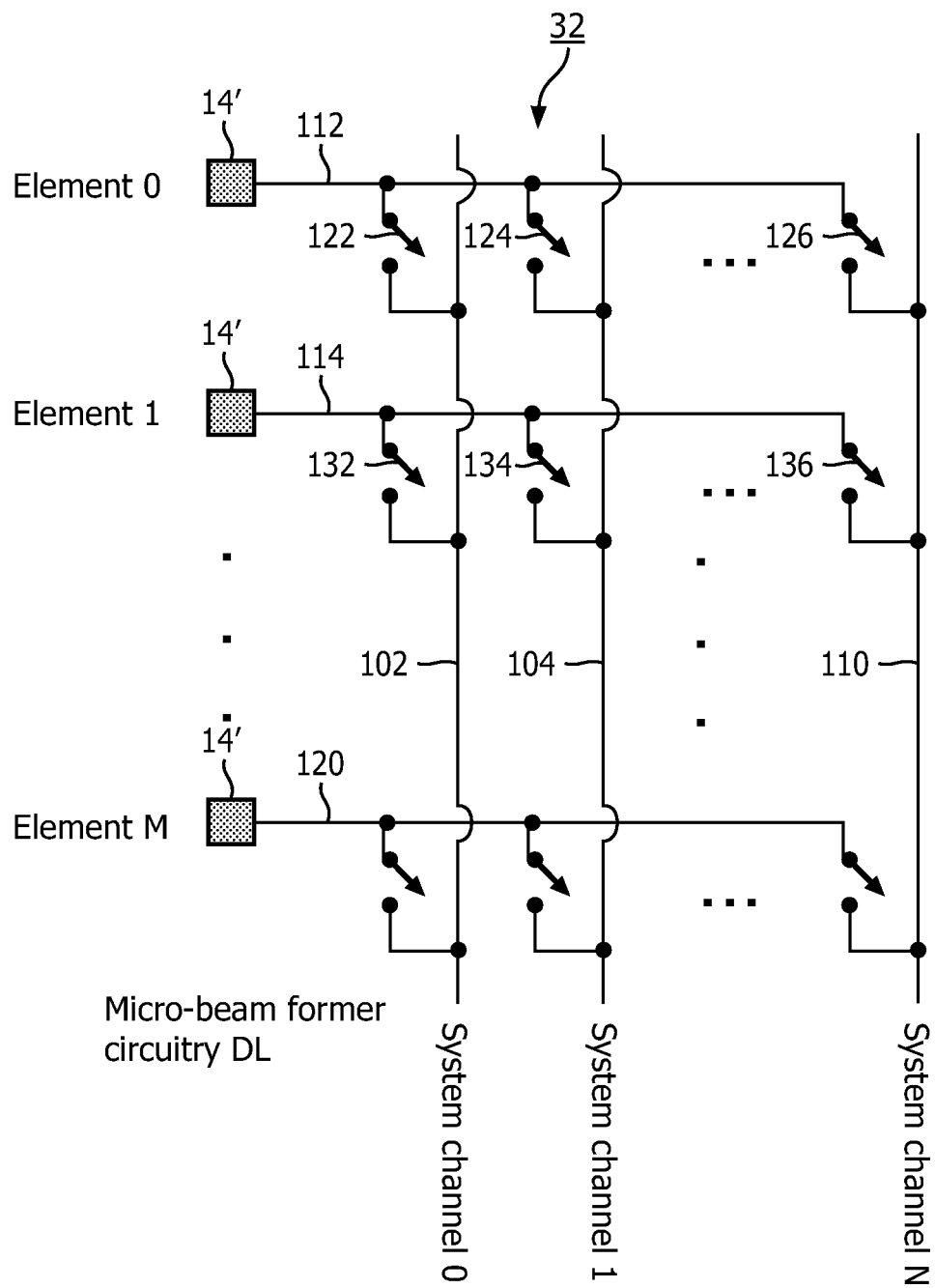
FIG. 4 illustrates a cross point switch matrix for coupling microbeamformed patches of a 2D array of various sizes to system beamformer channels in accordance with the principles of the present invention.

FIG. 4 illustrates a cross point switching matrix suitable for selectively coupling delayed signals from the probe microbeamformer 14 to conductors of the cable 16 and channels of the system beamformer 22. Each element of the 2D matrix array transducer, such as element 0, element 1, . . . element M is coupled to delay circuitry 14' of the microbeamformer 14 which imparts an appropriate delay to each received signal. Each delayed element signal is conducted by a line 112, 114, . . . 120 to arms of electronic switches such as 122, 124, . . . 126 and 132, 134, . . . 136. One of the electronic switches on the line is closed to couple the signal from that element to a selected system beamformer channel such as system channel 0, system channel 1, . . . system channel N. By selectively closing a desired switch in the cross point switching matrix, any delayed element signal can be put on a bus 102, 104, . . . 110 to sum with other signals on the bus and be applied to a cable conductor and thence to a channel of the system beamformer 22 for completion of the beamforming operation. The switch matrix 32 is thus able to direct the delayed signals of M transducer elements to N patch signal outputs 32, which are coupled by the cable 16 to the system beamformer 22.

The cable 16 of the probe, which may be a meter in length or more, terminates at a probe connector 36. The patch signal conductors of the cable terminate at pins of a connector block 38 of the probe connector 36. Located in the probe connector is an EPROM 50 which contains data identifying the probe and its particular characteristics (probe ID) to an ultrasound system to which the probe is connected. The EPROM 50 is also coupled to pins of the connector block 38. When the probe connector 36 is plugged into a mating connector of an ultrasound system 100 the connector block 38 is coupled to a mating block 138 of the system and patch signals are thereby connected to the system beamformer 22. A system beamformer controller 28 is coupled to the system beamformer 22 to control operation of the system beamformer. The system beamformer controller is also coupled to receive probe ID data from the probe's EPROM 50 which identifies the probe to the controller and enables the beamformer 22 to be set up for operation with the particular probe. The system beamformer controller in this example is further coupled to one or more conductors of the probe cable to supply information about the system beamformer to the matrix array probe. This system information is coupled to the microbeamformer controller 40 as indicated at 42 to enable the microbeamformer controller to set up the matrix array probe for operation with the ultrasound system to which it is connected.

Operation of the matrix array probe and ultrasound system of FIG. 3 is as follows. When the probe connector 36 is plugged into the ultrasound system 100, power from the ultrasound system powers the matrix array probe components. The EPROM provides probe ID information to the ultrasound system and the system now knows the type of probe that has been connected. Suppose as an example that the system beamformer 22 has 128 channels and that the matrix array probe 10 has 128 patch outputs 34, which are coupled to the connector block 38 by 128 patch signal conductors in the cable 16. Since the microbeamformer in this example has a maximum of 128 outputs 34 at which 128 delayed and summed patch signals can be produced, it can provide a maximum of 128 partially summed patch signals to the system beamformer for the completion of the beamforming process. This maximum number of partially summed patch signals can be processed by a system beamformer having 128 or more beamformer channels. In this example the system beamformer controller sets up the system beamformer to do final beamforming for 128 partial sum patch signals provided by the probe. The system beamformer controller 28 informs the probe by way of cable 16 and lines 42 that the system beamformer has 128 channels and the microbeamformer controller 40 responds by setting up the microbeamformer delays DL and the switches of the switch matrix 32 to provide 128 partial sum patch signals from all of the 128 outputs 34 to the system beamformer 22. Imaging then proceeds with 128 probe patches and patch output signals and 128 channel system beamformation.

Figure 5:
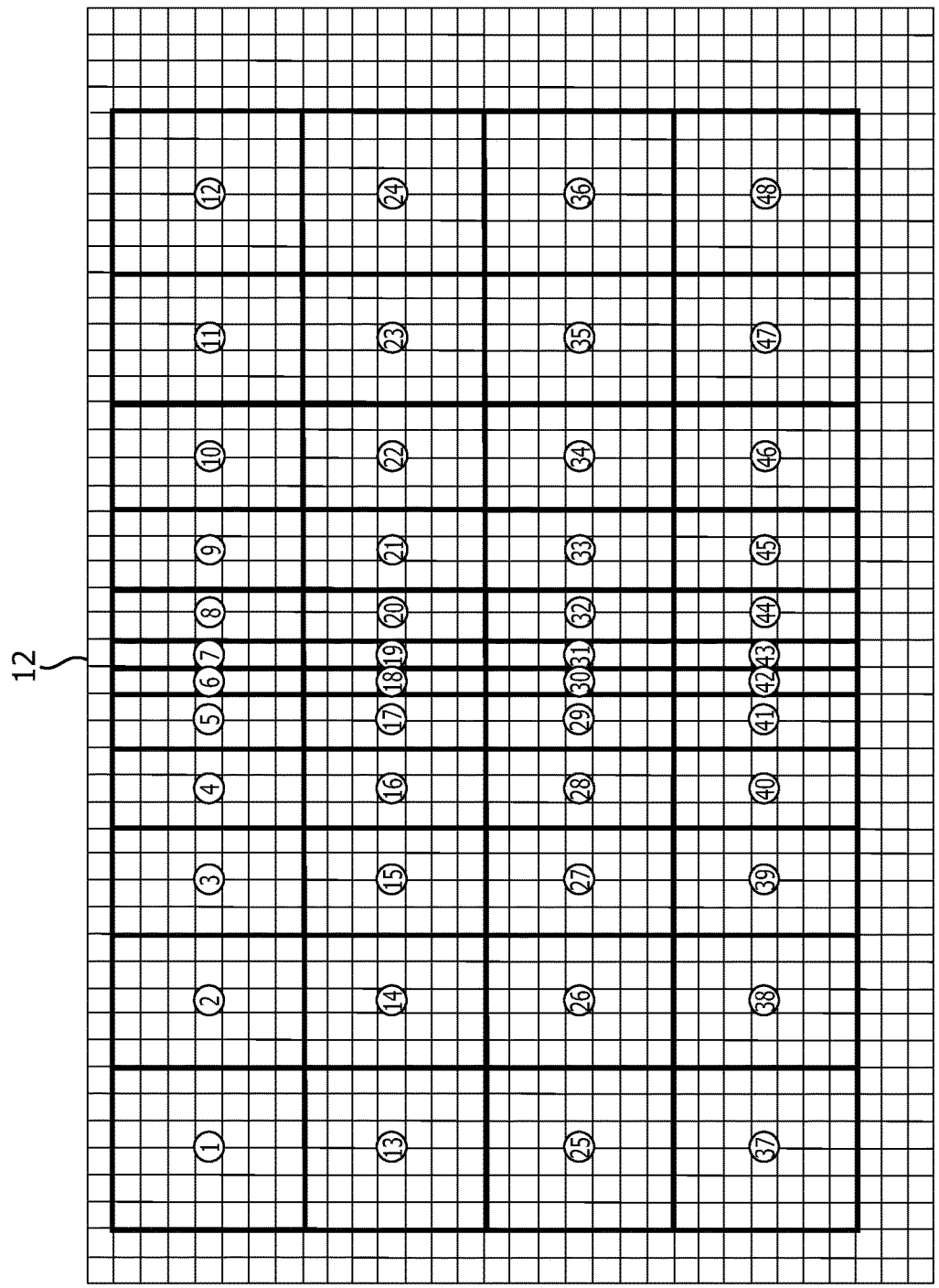
FIG. 5 illustrates a 2D matrix array transducer with differently sized patches for use with a 48-conductor cable or 48-channel system beamformer.

Suppose as another example that the ultrasound system 100 has a 48 channel system beamformer. The matrix array probe must now be configured to operate with this beamformer of fewer channels that the maximum of 128 patch output signals that the microbeamformer is capable of providing. The microbeamformer controller 40 is informed of the 48-channel system beamformer by way of lines 42 and responds by setting the switches of the switch matrix 32 so that partial sum patch signals for 48 patches are produced on 48 of the 128 outputs 34. The remaining outputs are not needed for patch signals. The delays of the delay lines DL for the array elements are set by delay control signals on lines 44 provided by the microbeamformer controller. The delays are appropriate for those of the 48 patches into which the elements of the 2D matrix array are grouped. One such 48 patch element configuration is shown in FIG. 5, which illustrates the use of 48 patches of different sizes. Smaller patches are located in the center of the array transducer and larger patches are on the lateral sides in the azimuth direction. The vertical dimension of the drawing is the elevation direction. The switches of the switch matrix 32 combine the individually delayed signals from the elements of each patch and couple the resultant partial sum signals on 48 of the outputs 34. The conductors of the cable which carry these 48 patch signals are coupled by the probe connector blocks 38 and 138 to the inputs of the 48 channels of the system beamformer 22. Imaging then proceeds with 48 channel system beamformation.

It is thus seen that when the matrix array probe of the present invention is to operate with a system beamformer having a channel count equal to or greater than the maximum number of patch signals that the matrix array probe can produce, the microbeamformer controller sets the delays and summing of delayed signals to produce its maximum number of patch signals which are coupled to the system beamformer for the completion of beamformation. When the matrix array probe is to operate with a system beamformer having a channel count which is less than the maximum, the microbeamformer controller sets the delays and summing of delayed signals to produce a number of partially beamformed patch signals which is less than the maximum.

Figure 6:
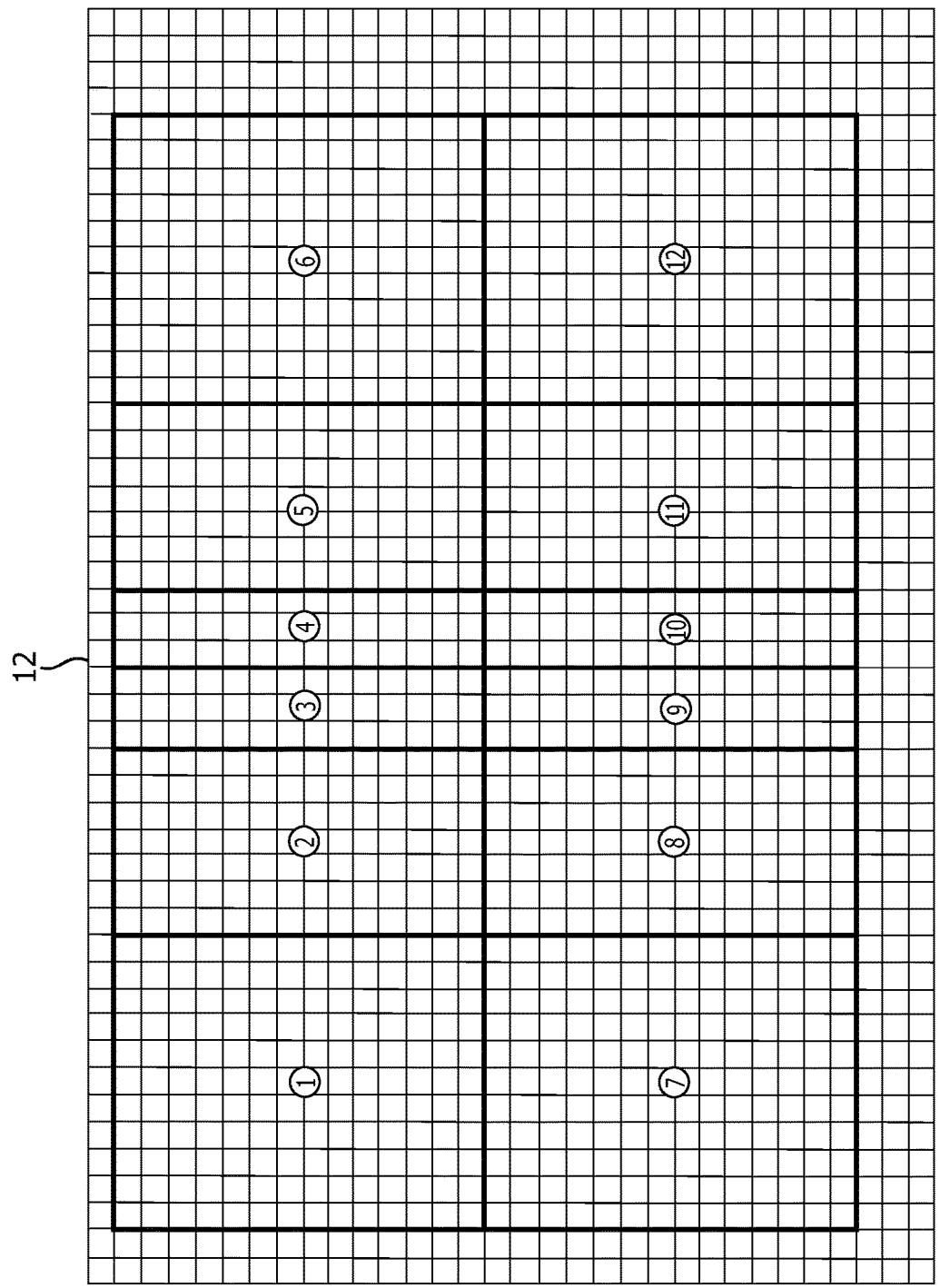
FIG. 6 illustrates a 2D matrix array transducer with differently sized patches for use with a 12-conductor cable or 12-channel system beamformer.

FIG. 6 illustrates a patch configuration of the matrix array transducer 12 when only twelve patches are needed for a 12-channel system beamformer. In that case, the delays and the switch matrix are set to provide twelve partial sum patch signals on twelve of the switch matrix outputs 34. The twelve patch signals are conducted over the cable 16 and applied to the channel inputs of a 12-channel system beamformer. FIG. 7 illustrates another matrix array patch configuration in which all of the elements of the 2D array 12 are grouped into eight uniformly sized patches. The delay lines DL and the switch matrix 32 then produce eight patch signals on eight of the 128 ("N") switch matrix outputs and cable conductors which are applied to the eight channel inputs of an 8-channel system beamformer.

While the matrix array probe of FIG. 3 is seen to be capable of operating with a variety of different system beamformers, it may alternatively be desirable to configure a matrix array probe for use with only one system beamformer. This can be done with most of the same probe components shown in FIG. 3, in particular with the same matrix transducer array and microbeamformer stack. Thus, the same transducer stack can be used for different probes for different ultrasound systems. A dedicated probe configuration can also provide a cost-reduced matrix array probe. It is frequently the case that the probe cable is the most expensive component of the probe, with the cost scaling with the number of conductors in the cable. If the matrix array probe is intended to be used strictly with an 8-channel system beamformer, for example, only eight signal conductors are needed in the cable for the patch signals, not 128 signal conductors. The complete matrix array probe cost is reduced by using a cable with only eight patch signal conductors instead of a full complement of 128 conductors.

Figure 8:
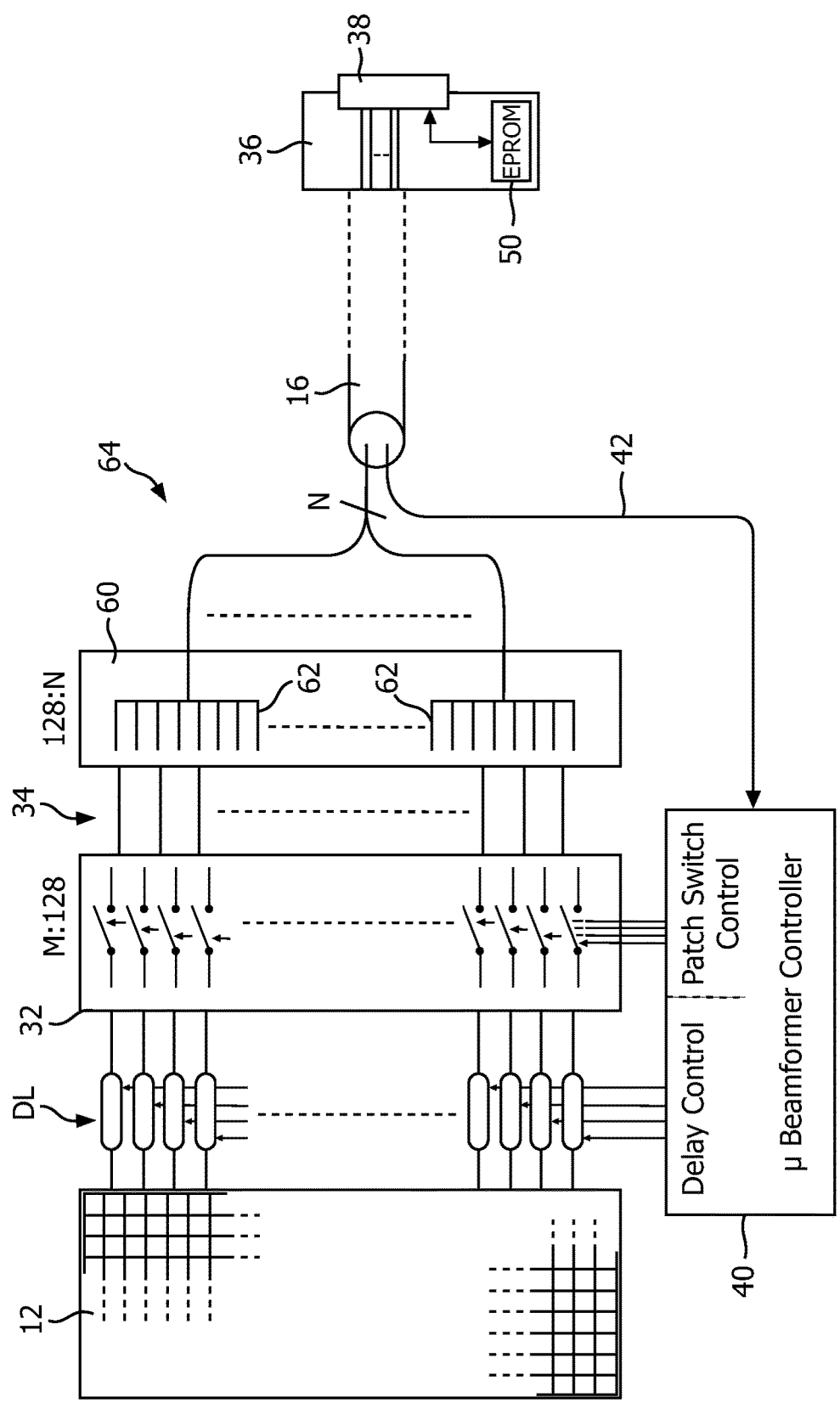
FIG. 8 illustrates a second example of a microbeamformer matrix array probe and ultrasound system constructed in accordance with the principles of the present invention which is hardwired for a predetermined number of cable conductors or system beamformer channels.

A transducer stack with a switch matrix such as switch matrix 32 of FIG. 3 can be used with a variety of different system beamformers by configuring the switches of the matrix 32 so that the M:N combining of delayed signals from the M elements of the matrix array to the N patch output signals results in the final desired number of patch signal outputs. For instance, N can be 8, 16, 48, or any other number of patch outputs matching the number of channels of the system beamformer. It is also possible to use the same 128-output switch matrix by partitioning the signal combining in two stages, with the switch matrix 32 producing 128 patch signals which are then further combined to the final lesser number of desired patch signals by a second signal combiner. When the matrix array probe is to only operate with one system beamformer configuration this second signal combiner can be a hard-wired signal combiner 60 as shown in FIG. 8. The hardwired signal combiner 60 can be a printed circuit board or flex circuit where signals are combined by connected traces 62 of the p.c.b. or flex circuit, for instance. The number of connected traces 62 produces the final number of desired patch signals at outputs 64. In the matrix array probe of FIG. 8 the switch matrix 32 does M:128 signal combining to the 128 outputs 34 of the switch matrix 32, and the second signal combiner 60 further reduces the number of patch signals by combining 128 patch signals to produce the final desired fixed number of patch signals N. For instance, if the matrix array probe of FIG. 8 is to operate with only an 8-channel system beamformer, the second signal combiner 60 would have eight sets of connected traces 62 producing eight patch outputs 64. The eight patch outputs 64 are coupled to the N patch signal conductors of the cable 16, where N is eight. When the probe connector 36 is plugged into an ultrasound system with an 8-channel system beamformer the eight patch signals conducted through the cable are connected to the eight channels of the system beamformer. A family of probes for different channel count system beamformers can thus be constructed using the same matrix array transducer 12, delay lines DL, switch matrix 32 and microbeamformer controller 40 in each probe, but with a different hard-wired second signal combiner 60 and probe cable for the number of channels of each different system beamformer. The same transducer stack can thus be used in each probe with an inexpensive hard-wired combiner and reduced conductor cable matched to the system beamformer channel configuration. Different probe connectors 36 and reduced pin count connector blocks 38 can also be employed for further cost reduction if desired.

Figure 9A:
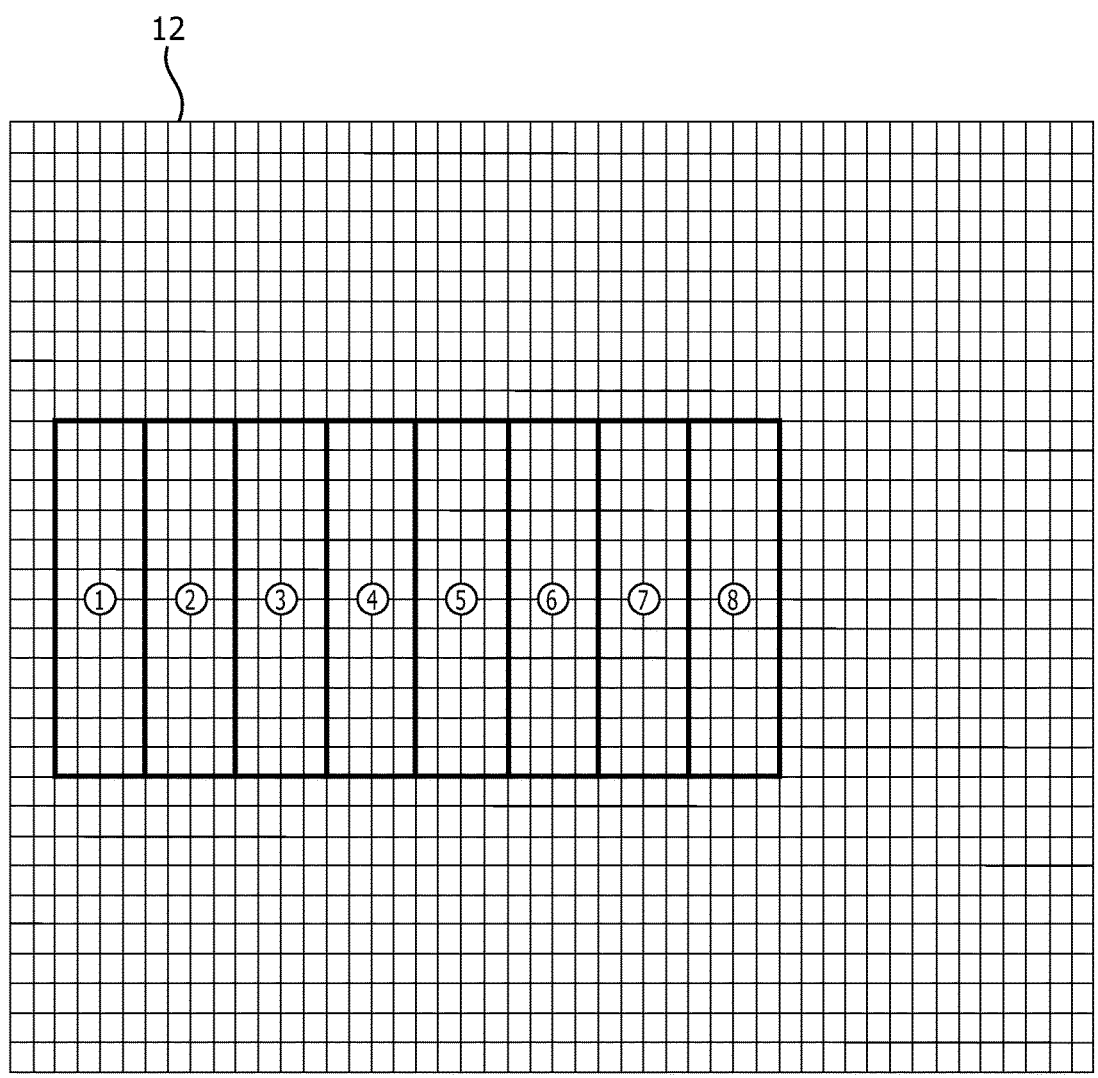
FIG. 9a illustrates a 2D matrix array transducer with a first aperture of eight uniformly sized patches.
Figure 9B:
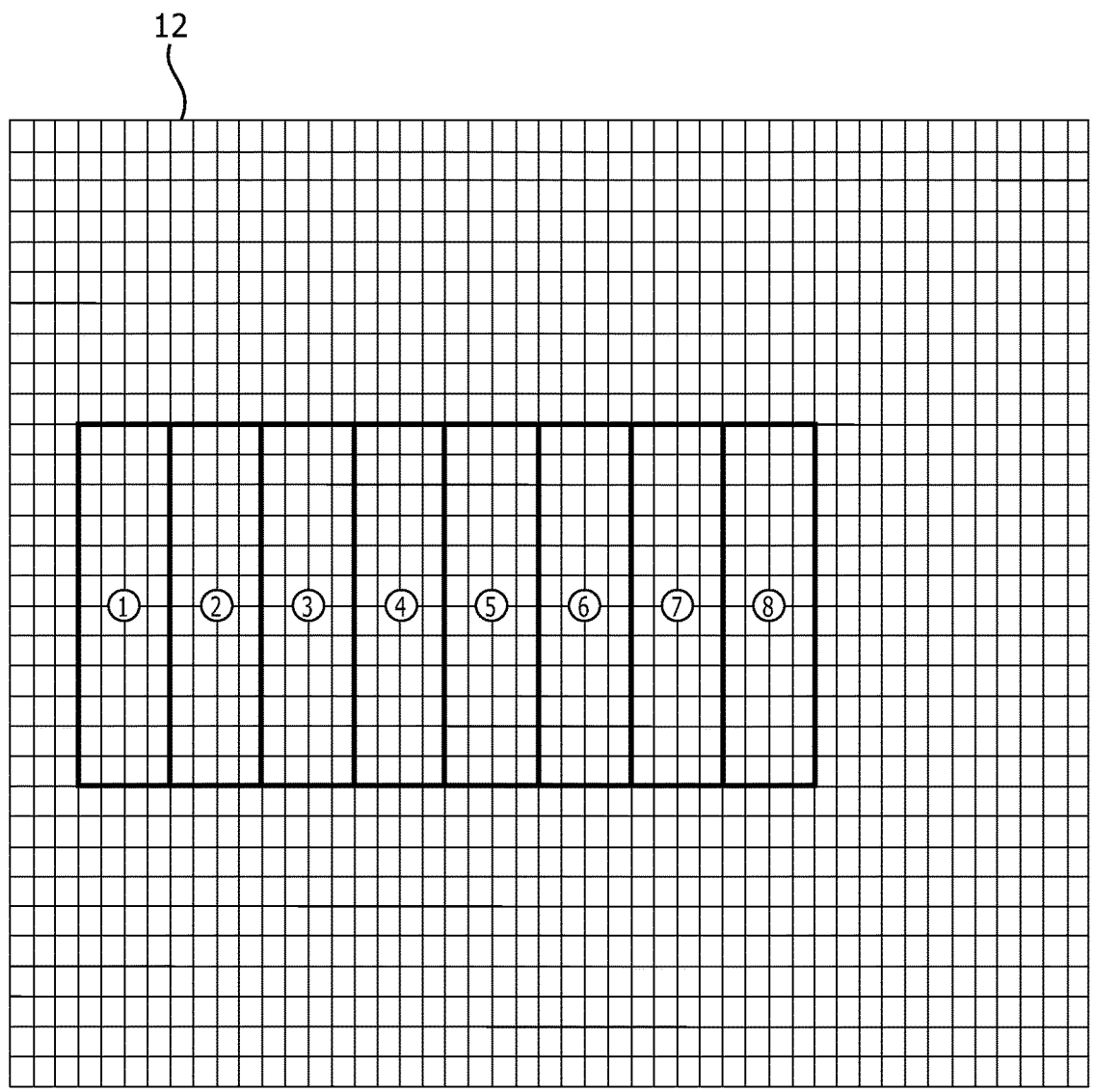
FIG. 9b illustrates the 2D matrix array transducer of FIG. 9a after translation of the aperture of FIG. 9a to a different position on the array.

FIGS. 9a and 9b illustrate patch configurations for a matrix array probe constructed as shown in FIG. 8. These configurations illustrate the use of eight patches on the matrix array 12 for use with an 8-channel system beamformer. Each of the eight patches is comprised of 48 transducer elements in this example, a total of 384 elements in the active aperture of eight patches of a 1536-element matrix array 12. The delays of the delay lines DL are adjusted for the patch sizes and locations and the switches of the switch matrix 32 are set to combine delayed signals from three transducer elements on each of the 128 outputs of the switch matrix. The switch matrix thus provides M:128 delayed signal combining, where M is the 384 elements of the eight patches. The second, hard-wired combiner 60 then performs 128:N combining where N is eight, combining sixteen of the switch matrix outputs 34 into one final patch signal at an output 64. The eight patch signals are then conducted over eight patch signal conductors of the cable 16 (N=8), for the completion of beamformation in the 8-channel system beamformer.

FIG. 9b shows the same aperture of eight patches but with the aperture shifted two elements to the right. The active aperture is translated across the array in this manner in the elevation direction to do linear array scanning. To scan with this relocated aperture, the delays DL and switches of the switch matrix must be set for the new, translated location of the patches. Once the delays and switches of the matrix 32 have been set for the new patch locations, another beam is transmitted and received from the new aperture location and the second combiner 60 does 128:8 combining as before to provide eight new patch signals to the system beamformer. Not only can the aperture be changed from beam to beam as shown in FIGS. 9a and 9b, the aperture can also be changed during the reception of a beam to grow the aperture with signal reception from increasing beam depths as described in my U.S. patent application Ser. No. 61/644,524, filed May 9, 2012, the contents of which are incorporated herein by reference.

What is claimed is:

1. An ultrasonic matrix array probe comprising:
   a matrix array of transducer elements;
   a microbeamformer coupled to the transducer elements of the matrix array, the microbeamformer comprising:
      a plurality of patch outputs;
      a plurality of controllable delays coupled to elements of the matrix array to produce differently delayed transducer signals; and
      a switch matrix comprising a plurality of controllable switches operable to:
         couple any one of the differently delayed transducer signals to any one of the plurality of patch outputs; and
         combine the differently delayed transducer signals to form a plurality of patch signals at the plurality of patch outputs, each of the plurality of patch signals corresponding to a patch including a set of the transducer elements, wherein the microbeamformer is configured to produce a maximum number of patch signals;
   a microbeamformer controller coupled to control the plurality of controllable delays and the plurality of controllable switches in the switch matrix;
   a probe connector which connects the ultrasonic matrix array probe to a system beamformer of an ultrasound system, the system beamformer having a given number of system beamformer channels; and
   a probe cable coupled to the plurality of patch outputs of the microbeamformer and the probe connector which couples the plurality of patch signals to the system beamformer,
   wherein the microbeamformer controller controls the plurality of controllable delays and the plurality of controllable switches to adjust sizes of patches and a number of patch signals based at least on the given number of system beamformer channels, wherein the microbeamformer controller is configured to produce the maximum number of patch signals when the given number of system beamformer channels equals or exceeds the maximum number of patch signals, and to produce a number of patch signals which is equal to or less than the given number of system beamformer channels when the given number of system beamformer channels is less than the maximum number of patch signals.

2. The ultrasonic matrix array probe of claim 1, wherein the microbeamformer controller is further coupled to receive a signal by means of the probe cable which identifies the number of patch signals to be produced by the microbeamformer.

3. The ultrasonic matrix array probe of claim 1, wherein the the microbeamformer controller is further configured to receive a signal which identifies the given number of system beamformer channels, and wherein the microbeamformer controller is configured to produce the number of patch signals and the patch sizes based at least on the received signal, and wherein the patches are not uniformly sized.

4. The ultrasonic matrix array probe of claim 3, wherein the signal which identifies the given number of system beamformer channels is produced by a system beamformer controller and is coupled to the microbeamformer controller by way of the probe connector and the probe cable.

5. The ultrasonic matrix array probe of claim 1, further comprising a memory device which stores information about the ultrasonic matrix array probe, wherein the information about the ultrasonic matrix array probe is coupled to the ultrasound system when the probe connector connects the matrix array probe to the system beamformer.

6. The ultrasonic matrix array probe of claim 1, wherein the probe cable further comprises a plurality of patch signal conductors which is equal to the number of patch signals produced by the microbeamformer under control of the microbeamformer controller.

7. The ultrasonic matrix array probe of claim 1, wherein the maximum number of patch signals is 128.

8. The ultrasonic matrix array probe of claim 7, wherein the given number of system beamformer channels is 48 or less.

9. An ultrasonic matrix array probe comprising:
a matrix array of transducer elements;
a microbeamformer coupled to the transducer elements of the matrix array, the microbeamformer comprising:
  a plurality of patch outputs;
  a plurality of controllable delays coupled to elements of the matrix array to produce differently delayed transducer signals; and
  a switch matrix comprising a plurality of controllable switches operable to:
    couple any one of the differently delayed transducer signals to any one of the plurality of patch outputs; and
    combine the differently delayed transducer signals to form a given number of patch signals at the plurality of patch outputs;
a microbeamformer controller coupled to control the plurality of controllable delays and the plurality of controllable switches in the switch matrix;
a probe connector which connects the ultrasonic matrix array probe to a system beamformer of an ultrasound system, the system beamformer having a number of beamformer channels;
a signal combiner coupled to receive the given number of patch signals and configured to combine the given number of patch signals to produce a fixed number of patch output signals based at least on the number of beamformer channels, wherein the fixed number of patch output signals is equal to the given number of patch signals when the number of beamformer channels exceed the given number of patch signals, and the fixed number of patch output signals is equal to or less than the number of beamformer channels when the number of beamformer channels is equal to or less than the given number of patch signals; and
a probe cable coupled to the microbeamformer and the probe connector which couples the fixed number of patch output signals to the system beamformer.

10. The ultrasonic matrix array probe of claim 9, further comprising a memory device which stores information about the ultrasonic matrix array probe, wherein the information about the ultrasonic matrix array probe is coupled to the ultrasound system when the probe connector connects the ultrasonic matrix array probe to a system beamformer.

11. The ultrasonic matrix array probe of claim 9, wherein the probe cable further comprises a plurality of patch signal conductors which is equal to the fixed number of patch output signals produced by the microbeamformer.

12. The ultrasonic matrix array probe of claim 9, wherein the given number of patch signals is 128, and wherein the number of beamformer channels is 48 or less.

* * * * *